United States Patent [19]
Pope et al.

[11] Patent Number: 5,888,374
[45] Date of Patent: Mar. 30, 1999

[54] IN-SITU PROCESS FOR THE MONITORING OF LOCALIZED PITTING CORROSION

[75] Inventors: Daniel H. Pope, Georgetown, Tex.; YuPo J. Lin, Westmont, Ill.; Edward J. St. Martin, Libertyville, Ill.; James R. Frank, Glen Ellyn, Ill.

[73] Assignee: The University of Chicago, Chicago, Ill.

[21] Appl. No.: 855,707

[22] Filed: May 8, 1997

[51] Int. Cl.$^6$ .................................................. G01N 27/26
[52] U.S. Cl. ....................... 205/775.5; 204/404; 205/777
[58] Field of Search ....................... 204/404; 205/775.5, 205/776, 776.5, 777

[56] References Cited

U.S. PATENT DOCUMENTS

| | | | |
|---|---|---|---|
| 4,575,678 | 3/1986 | Hladky | 324/425 |
| 5,139,627 | 8/1992 | Eden et al. | 204/153.11 |
| 5,151,163 | 9/1992 | Miller | 205/776.5 |

FOREIGN PATENT DOCUMENTS

| | | |
|---|---|---|
| 2118309 | 10/1983 | United Kingdom . |
| WO 94/12862 | 6/1994 | WIPO . |

*Primary Examiner*—T. Tung
*Attorney, Agent, or Firm*—Mason, Kolehmainen, Rathburn & Wyss

[57] ABSTRACT

A method and apparatus are provided for monitoring localized pitting corrosion in metal pipes or storage vessels. Electrochemical probes are used for sensing electrochemical noise voltage values and electrochemical noise current values. The root-mean-square electrochemical noise current and voltage values are calculated and stored for the sensed electrochemical noise voltage values and the electrochemical noise current values. The stored electrochemical noise current and voltage values are processed by transforming the stored electrochemical noise current and voltage values into power spectral density data utilizing a fast Fourier transform. A slope of the power spectral density data relative to frequency is calculated. The electrochemical probes include a pair of working electrodes formed of the same material of the monitored metal pipes or storage vessels and a reference electrode formed of a corrosion resistant material. A linear slope of a low-frequency portion of the power spectral density data is calculated by using a least-square method.

12 Claims, 5 Drawing Sheets

IN-SITU PROCESS FOR THE MONITORING OF LOCALIZED PITTING CORROSION

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to corrosion monitoring systems, and more particularly to, methods and apparatus for monitoring localized pitting corrosion in metal pipes or storage vessels.

DESCRIPTION OF THE PRIOR ART

Metal corrosion is a major and costly problem for many industries. Two basic kinds of corrosion can be identified. General corrosion occurs uniformly over the entire surface of a metal structure and the rate of this form of corrosion can be easily monitored and predicted. Localized corrosion, however, is a more serious form of corrosion where rapid and sustained localized metal pitting occurs. This localized pitting can lead to the premature and catastrophic failure of metal pipes and storage vessels. It can shorten the material life time by orders of magnitude as compared with generally uniform corrosion. Early detection of localized corrosion would result in cost savings because metal parts could be treated, repaired or replaced only when necessary thus avoiding unscheduled failures.

For years, engineers have been trying to develop effective monitoring methods to detect localized pitting corrosion. Among the innovative methods that were evaluated, electrochemical noise analysis (ENA) is recognized as one of the potential monitoring techniques. For example, U.S. Pat. No. 4,575,678 issued Mar. 11, 1986 discloses corrosion monitoring apparatus and corrosion monitoring method utilizing electrochemical noise analysis.

Electrochemical noise analysis is a non-destructive, in-situ monitoring method of the natural corrosion process that measures the electrochemical corrosion current and potential fluctuations. However, due to the chaotic nature of the corrosion process, signal processing of the recorded current and potential noise becomes very critical in determining the meaning of the recorded data.

Researchers have been interpreting the electrochemical noise analysis data by using different signal processing algorithms to quantitatively or qualitatively characterize the corrosion process. In an effort to specify the corrosion mechanisms and distinguish between uniform and localized pitting corrosion, they have monitored the signals for potential and current noise levels, noise resistance and pitting index (i.e., standard deviation of current noise divided by average current noise). However, it was found that with these results alone they can not effectively identify the different corrosion mechanisms.

A principal object of the present invention is to provide an improved method and apparatus for monitoring localized pitting corrosion in metal pipes or storage vessels.

It is another object of the present invention to provide such an improved method and apparatus for monitoring localized pitting corrosion in metal pipes or storage vessels that utilizes electrochemical noise analysis.

It is another object of the present invention to provide such an improved method and apparatus for monitoring localized pitting corrosion in metal pipes or storage vessels that utilizes electrochemical noise analyzed in the frequency domain, utilizing a Fourier transform of electrochemical noise data.

It is another object of the present invention to provide such an improved method and apparatus for monitoring localized pitting corrosion in metal pipes or storage vessels that utilizes electrochemical noise analyzed in the frequency domain, utilizing a Fourier transform of electrochemical noise data to provide a power spectral density, and utilizing a slope of the power spectral density versus frequency to identify localized pitting corrosion.

It is another object of the present invention to provide such an improved method and apparatus for monitoring localized pitting corrosion in metal pipes or storage vessels that utilizes electrochemical noise data obtained with a plurality of electrochemical probes including a generally non-corroding reference electrode.

It is another object of the present invention to provide such an improved method that overcomes many of the disadvantages of prior art arrangements.

SUMMARY OF THE INVENTION

In brief, these and other objects and advantages of the invention are provided by a method and apparatus for monitoring localized pitting corrosion in metal pipes or storage vessels. Electrochemical probes are used for sensing electrochemical noise voltage values and electrochemical noise current values. The root-mean-square electrochemical noise current and voltage values are calculated and stored for the sensed electrochemical noise voltage values and the electrochemical noise current values. The stored electrochemical noise current and voltage values are processed by transforming the stored electrochemical noise current and voltage values into power spectral density data utilizing a fast Fourier transform. A slope of the power spectral density data relative to frequency is calculated.

In accordance with features of the invention, the electrochemical probes include a pair of working electrodes formed of the same material of the monitored metal pipes or storage vessels and a reference electrode formed of a corrosion resistant material. A linear slope of a low-frequency portion of the power spectral density data is calculated by using a least-square method.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

The improved method of the invention is used for monitoring local pitting corrosion in steel pipes or storage vessels. The pitting corrosion is generally due to microbial attack, which can be treated with biocides once detected. Established practice is to place a probe containing three electrodes, whose composition is identical to that of the pipe, in the area where pitting corrosion may be expected to occur. Electrochemical noise analysis (ENA) of the electrochemical noise created by the corrosion can, when properly analyzed in accordance with the method of the invention, indicate the presence of pitting corrosion. The spectrum of the electrochemical noise is analyzed in the frequency domain by Fourier analysis to give a power spectral density (PSD). The slope of PSD versus frequency relates to the corrosion mechanism. Pitting corrosion is characterized by very low frequencies. The present invention provides improvements over the earlier methods of analysis through the use of the improved probe 102 and analysis of signals to cover the very low frequencies. To generate the PSD versus frequency slopes, electrochemical currents and voltages are measured at short time intervals for a long period of time and then analyzed. A feature of this analysis is the ability to screen out the high frequency noise attributed to general corrosion thereby amplifying the low frequency signals denoting pitting.

Figure 1:
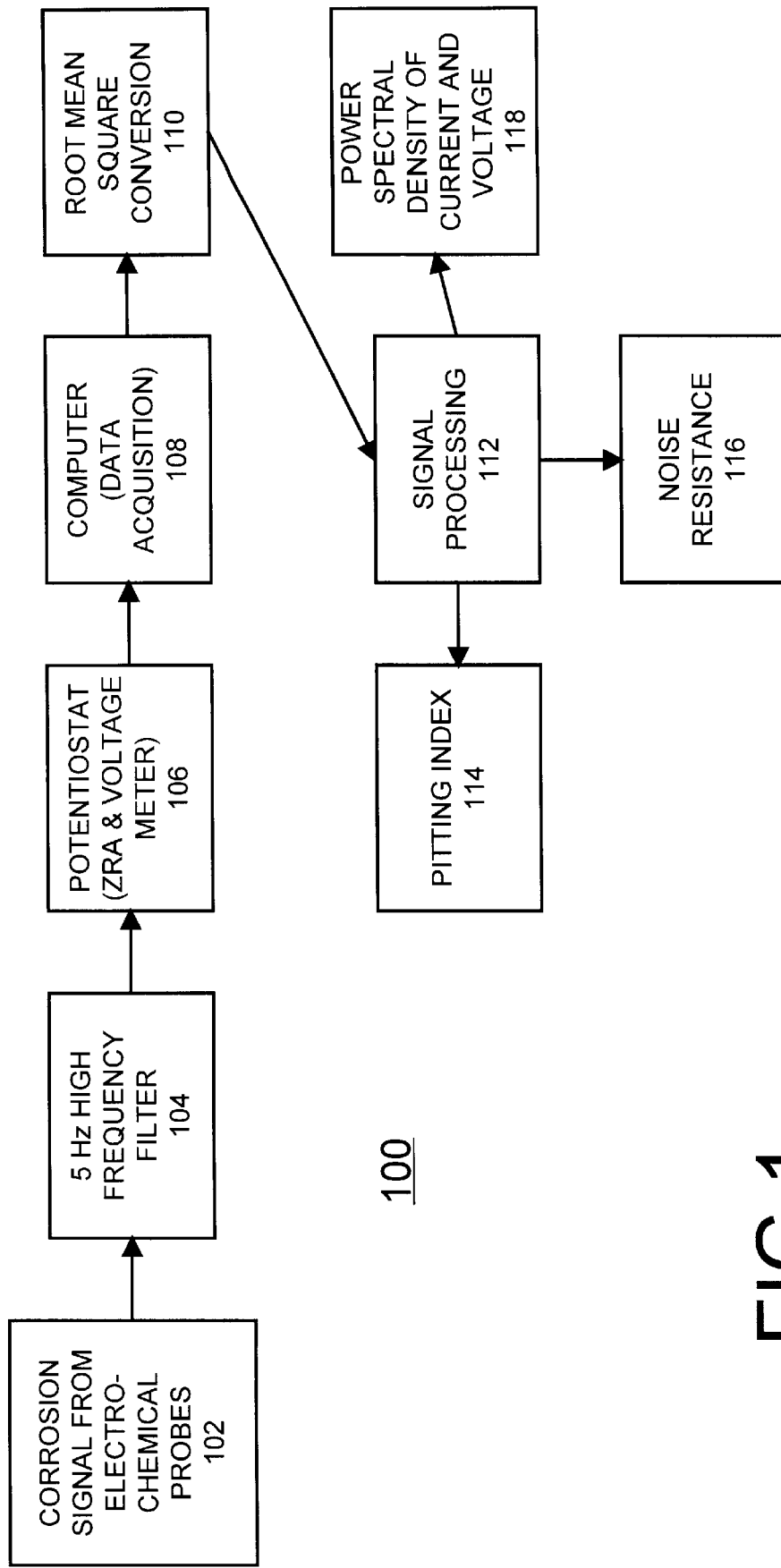
FIG. 1 is a schematic and block diagram representation of an electrochemical noise monitoring system in accordance with the present invention.
Figure 2A:
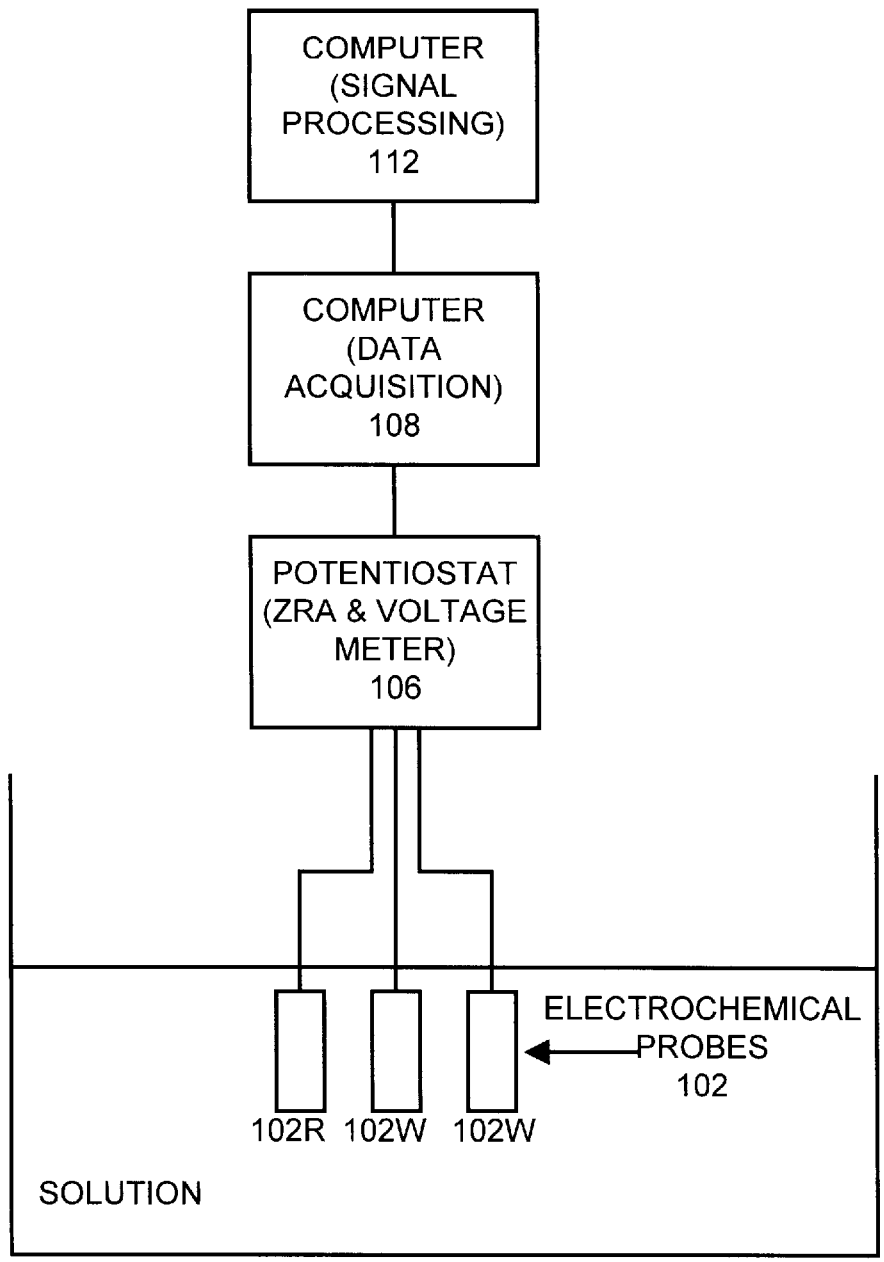
FIGS. 2A and 2B are schematic and block diagram representations illustrating components including the electrochemical probes of the electrochemical noise monitoring system of FIG. 1.
Figure 2B:
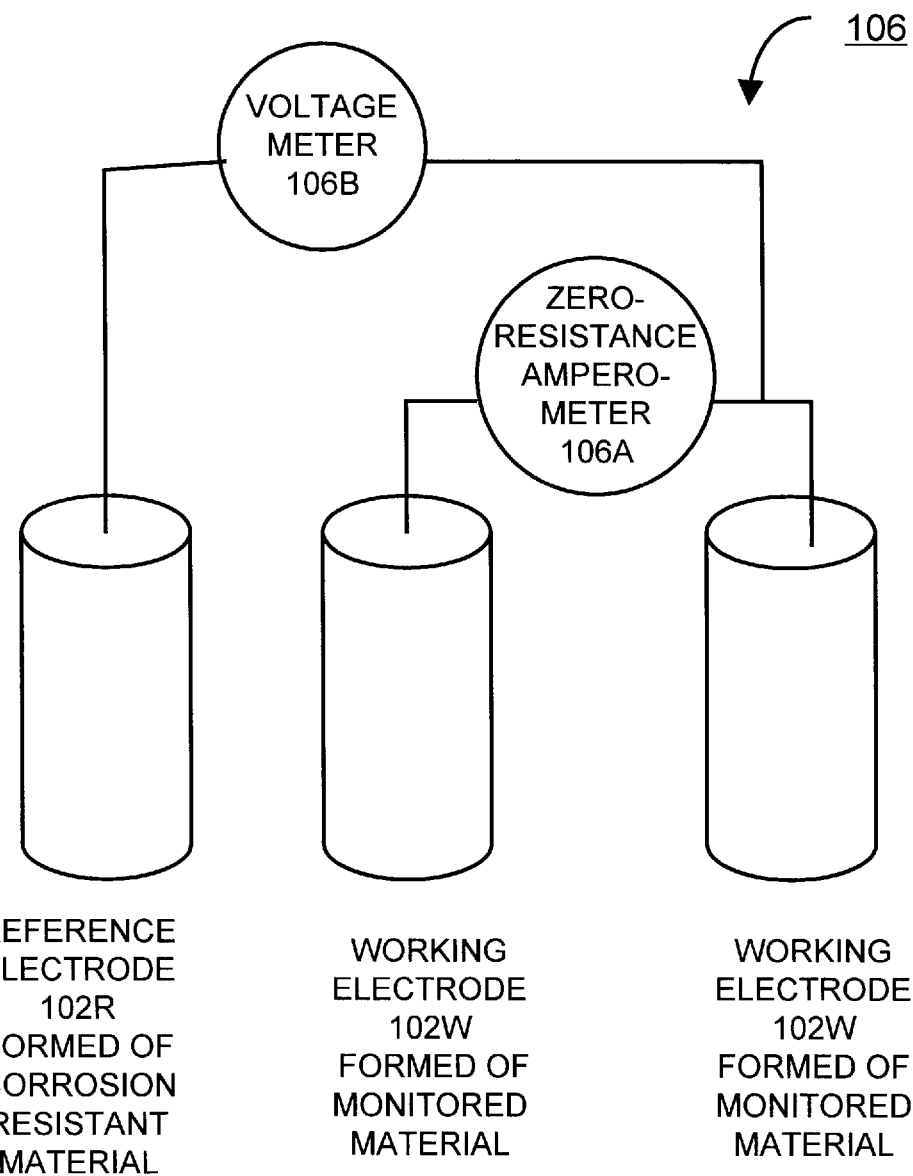

Having reference now to the drawings, in FIGS. 1, 2A and 2B, there is shown an electrochemical noise monitoring system in accordance with the present invention generally designated by the reference character 100. A detected corrosion signal from a plurality of electrochemical probes 102 is applied to a 5 Hz high frequency filter 104. The filtered corrosion signal output of filter 104 is applied to a potentiostat 106. The electrochemical probes 102 are connected to the potentiostat 106 which serves as a zero-resistant amperometer (ZRA) 106A and a high impedance voltage meter 106B. The signals recorded by the potentiostat 106 are stored in the computer by a computer data acquisition function 108. A root-mean square (RMS) conversion of the sensed data is provided by a root-mean square conversion block 110. The stored RMS current noise data and RMS voltage noise data are processed later using a signal processing function software 112 provided by the same computer of monitoring system 100.

Referring to FIGS. 1 and 2A, the signal output of the potentiostat (ZRA and voltage meter) 106 is applied to the computer data acquisition function 108 and the root mean square conversion function 110 is applied to the sensed electrochemical voltage and current noise data. The calculated root-mean-square value of current and voltage, called the root-mean-square (RMS) current noise or voltage noise, are saved in a data file along with the average current level. The signal processing function 112 calculates a pitting index 114, a noise resistance 116 and a power spectral density of current and voltage 118.

As shown in FIG. 2B, the potentiostat 106 includes a zero-resistance amperometer (ZRA) 106A and a voltage meter 106B. The two electrodes 102W in the electrochemical noise probe 102, called the working electrodes 102W, are shorted and connected through the zero-resistance amperometer 106A. The electrode 102W on which the electrochemical reaction of interest does not occur is also called a counter electrode. The third electrode 102R, called the reference electrode 102R, is parallel connected with the other electrodes via the voltage meter 106B. The working electrodes 102W are formed of the same material as the steel pipes or storage vessel to be monitored. The reference electrode 102R is formed of a non-corrosive or highly corrosion resistant material. Conventional or traditional electrochemical noise probes includes three identical material electrodes or probes used to measure the electrochemical noise. The non-corroding or very corrosion resistant material used for the reference electrode 102R in the electrochemical noise monitoring system 100 substantially avoids interference by an otherwise corroding reference electrode observed in traditional three-probe electrochemical noise measurement devices.

The electrochemical noise detecting system 100 for pitting corrosion measurements includes three major components including a personal computer, such as an IBM or Dell personal computer performing the data acquisition function 108 and signal processing function 112. The potentiostat 106 and electrochemical probes 102 can be provided with a PC plug-in potentiostat/PC interface card, such as a PC-3 interface card manufactured and sold by Gamry Instruments, Inc. and the three-electrode electrochemical probes 102, for example, manufactured and sold by Rohrback Cosasco, Inc.

In accordance with features of the invention, spectral analysis of the chaotic electrochemical noise (ECN) is applied. It has been shown that spectral analysis of the electrochemical noise provides a powerful signal processing algorithm with the potential to characterize the noise data. Spectral analysis of the electrochemical noise ECN is accomplished by converting the time series data of the potential and current signals into frequency domains by fast Fourier transform (FFT). The transformed signal is called a power spectral density (PSD). The slope of the PSD versus frequency is related to pitting corrosion. The frequency of noise signal generated by a progressive localized pitting corrosion has strong electrochemical characteristics. The frequency of the noise signal can decrease with the increase of pitting depth or the progress of localized pitting corrosion. Therefore, the data in the low frequency portion of the spectral analysis is used in the method of the invention in characterizing the corrosion process. Modifying the signal collection procedure to extend the frequency window of the spectral analysis to a lower frequency range, for example, $10^{-4} \sim 10^{-5}$ Hz improves the resolution of spectral analysis.

Figure 3A:
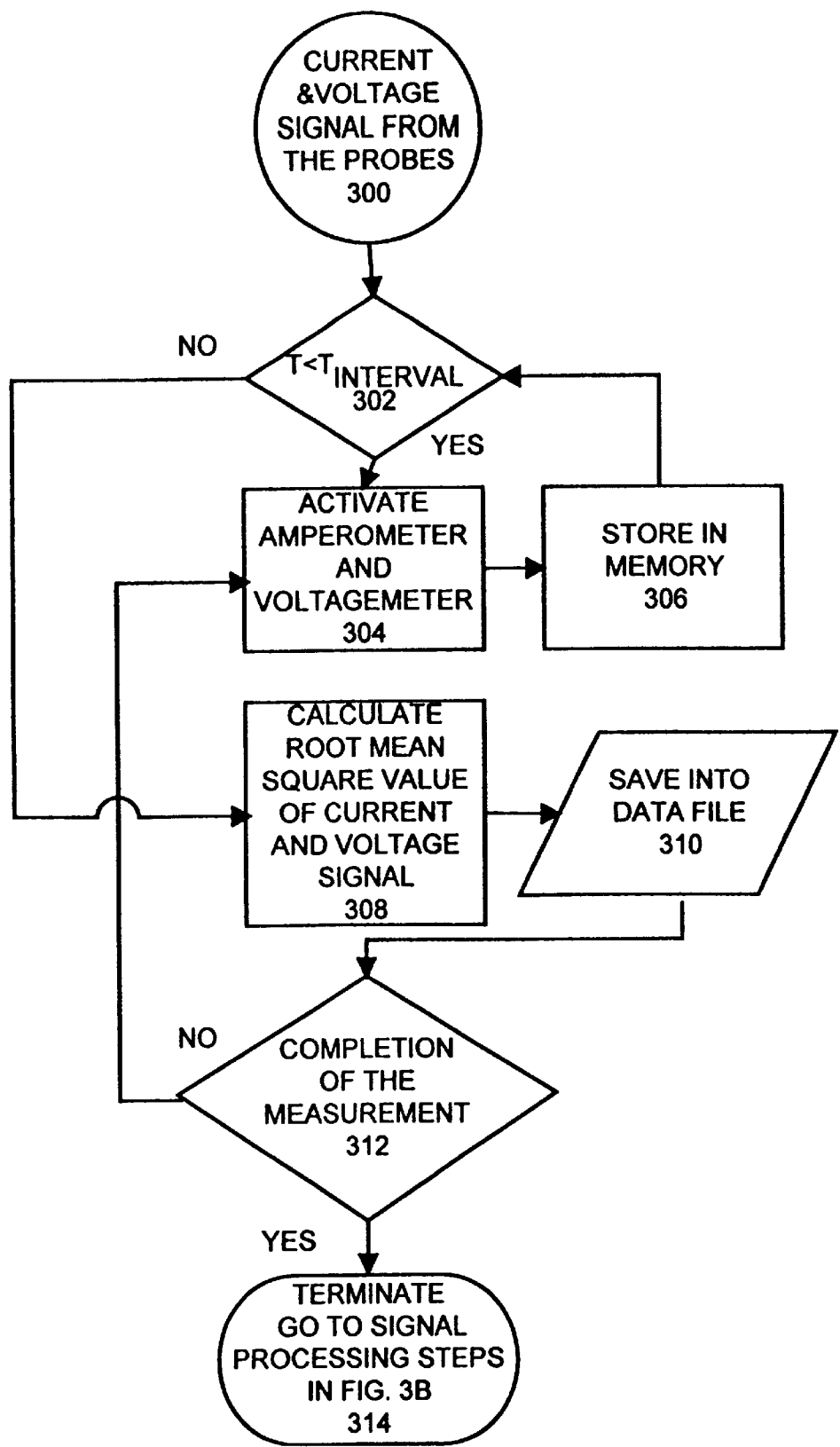
FIGS. 3A and 3B are flow charts illustrating sequential steps performed by the electrochemical noise monitoring system of FIG. 1 in accordance with the corrosion monitoring methods of the present invention.

During the corrosion monitoring method of the invention, as illustrated and described with respect to FIG. 3A, the potential and current signal levels are measured at short time intervals, for example, a fixed number of seconds to minutes, for a long period of time, for example, a fixed number of hours to days. Further signal processing of the data is performed, as illustrated and described with respect to FIG. 3B. The time series data is expressed as the standard deviation of the signal frequency distribution and thus represents the potential and current noise levels. These results are then converted by using a fast Fourier transform to obtain the power spectral density profile of the potential and current noise. The linear slope of the low-frequency portion of the PSD (called the α value), is calculated by linear fitting of the low-frequency portion of the PSD by using the least-square method. The new design of signal acquisition and processing improved the spectral analysis in two ways. The first is to extend the frequency window of the PSD to lower frequencies. The second is that the PSD analysis of potential and current noise levels works like a high frequency filter. It filters out the high frequency signal which, in general, is contributed by uniform corrosion. Therefore, it amplifies any low frequency signals, which could be contributed by the localized pitting corrosion process. This results in an improvement in sensitivity of PSD slope response to localized pitting corrosion.

Figure 3B:
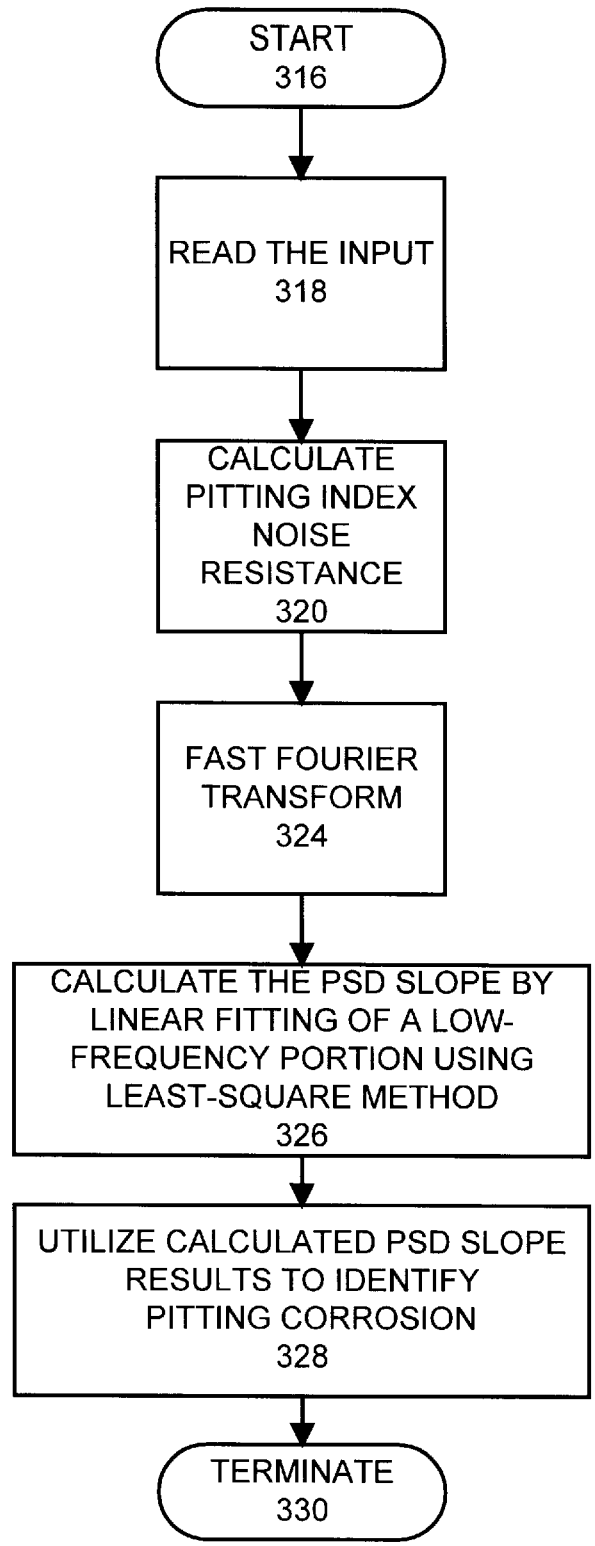

Having reference to FIGS. 3A and 3B, the current signal is measured by the zero-resistance amperometer 106A between the working electrodes 102W and the voltage signal is measured by the voltage meter 106B between the working and reference electrodes 102W and 102R as indicated at a block 300. The measured current noise signal and voltage noise signal are recorded for a short period of time, such as 4 seconds, identified as indicated at a decision block 302. The zero-resistance amperometer 106A and voltage meter 106B are activated as indicated at a block 304. The voltage and current noise readings are stored in memory as indicated at a block 306. The acquired multiple current and voltage data points, for example, 400 points are used to calculate the root mean square value of the current signal and voltage signal and the average current signal level acquired during the short period of time, such as 4 seconds. The calculated root-mean-square value of current and voltage, called the root-mean-square (RMS) current noise or voltage noise, along with the average current level are saved in a disk data file as indicated at a block 310. The steps are repeatedly executed at a first fixed time interval, such as 60 seconds until the total operating time reaches the time specified, for example, 60 hours identified as indicated at a decision block 312.

Referring to FIG. 3B, after one set of measurements is done, the signal processing software is executed starting at block 316. The input from the data file saved at block 310 in FIG. 3A, for example, with 3600 data points for each RMS current and RMS voltage noise is read as indicated at a block 318. The signal processing software 112 calculates the value for pitting index and noise resistance directly by using the data in the data file as indicated at a block 320. The same raw data from the data file, the RMS current noise and RMS voltage noise, is also converted via fast Fourier transform to obtain the power spectral density (PSD) of RMS voltage noise and RMS current noise as indicated at a block 324. Finally, the PSD slope of RMS voltage noise and RMS current noise are calculated using the least-square method as indicated at a block 326. Then calculated PSD slope results are utilized to identify pitting corrosion as indicated at a block 328 to complete the process as indicated at a block 330.

The results presented below are obtained from the study of galvanic corrosion in an aqueous system. A glass H-cell was used to carry out the experiments. The solution in the cell can be easily purged with oxygen or nitrogen gas in two different chambers of the cell. Three different electrode materials are used for the counter electrodes. They are platinum coated on titanium composite (Pt/Ti), stainless steel (S.S. 316) and glassy carbon (GC). The coupons used in the experiments were carbon steel samples (C1018). The selected counter electrodes are more noble than the carbon steel coupon, therefore, they serve as a rapid corrosion promoter. The new specimens were cleaned in an acid cleaning solution and rinsed with deionized water. After the water rinsing, the specimens were cleaned by sonication in water. The cleaned specimens were dipped into acetone and then dried in an oven to remove the water. To create the artificial rapid pitting corrosion, the coupon surface was deposited with several tiny agar drops. The agar was premixed with either 5 wt. % of NaCl and 4 wt. % of agar or by further adding 0.05 vol. % of concentrated HCl or acetic acid solution. The agar deposited coupon was put into oxygen purging deionized or tap water for corrosion studies. For each run of an agar-coated coupon, a no-agar-coated coupon was also tested in parallel. The test of the agar deposited coupons lasted from 45 hours to 100 hours. Electrochemical noise as well as weight loss measurements were made in each experiment.

The current noise was measured between the shorted counter electrode (oxygen or proton reduction) and the corroded coupon (iron oxidation) by a zero-resistance amperometer. The potential noise was measured by the reference electrode 102R without interfering with the corrosion process. The data acquisition software 108 includes the information of mean current for each measurement point of current noise. The signal processing program 112 was developed using Mathlab™ to calculate the pitting index (PI) at block 114, noise resistance (NR) at block 116 and the slope of potential and current noise power spectral density (PSD) at block 118. To calculate the slope index a data acquisition procedure was established. In the procedure, the current and potential fluctuation of corroding samples are read in a short period of time (e.g., 1 to 4 seconds) with consecutive 100 to 400 measurements (i.e., sampling rate of 0.01 s to 0.05 s). The linear standard deviation of these consecutive data points is calculated and the result is recorded in a data file. The measurement/calculation is repeated at every time interval (e.g., repeating time of 10 to 60 seconds) for a long period of time (e.g., total time of 20 to 100 hours). After the measurement, the data is converted by fast Fourier transform to obtain the power spectral density profile of the potential or current noise. The $\alpha$ value is calculated by linear fitting the low-frequency portion using the least-square method.

During the course of our research we have discovered that the power spectral density of potential noise level (PSDPNL) is a sensitive signal parameter to effectively differentiate localized pitting corrosion and general uniform corrosion The linear slope of the low-frequency portion of the PSDPNL can be used as an index to reveal the corrosion mechanism.

For general uniform corrosion, using the power spectral density of potential noise level of the uniform corrosion model, the PSD was maintained at a near constant level through out all the frequency range (i.e., the $\alpha$ value is closed to zero). This is because the general corrosion mechanism in nature is a random process. Therefore, its PSD is independent of the frequency. The average $\alpha$ value (the slope) of PSDPNL measured using different samples with general, uniform corrosion are summarized in Table 1.

The PSDPNL of localized pitting corrosion sample with four deep pits resulted in the PSD curve including a linear decline in the low-frequency portion with a slope equal to −40 dB/decrease ($\alpha$=40). The linear decline in the low frequency range is due to the dominating process of localized pitting corrosion on the entire surface. It changes the corrosion mechanism to a deterministic process instead of a random process. The average slopes of PSDNL of samples with natural pitting corrosion are summarized with their electrochemical noise monitoring results in the following Table 2.

Accelerated Pitting Corrosion: The average $\alpha$ values of PSDPNL measured using the artificial accelerated pitting corrosion model provided average $\alpha$ values in the range of 25~30 dB/decade. They are all substantially higher than the $\alpha$ values measured using the uniform corrosion samples. The departure of $\alpha$ value from the 40 dB/decade level is due to the large number of pits formed near the artificial pitting area. Because of the large increase in the number of pitting sites on the coupon surface, the deterministic signal created by the localized pitting corrosion process is diminished slightly and starts to shift into a random signal. Table 3 summarizes the electrochemical noise monitoring results of this set of samples.

In order to verify the observation of accelerated pitting corrosion as described above, another series of experiments were carried out. Instead of using corrosion promoting coupons as in the previous experiment, commercial probes and electrodes (obtained from Rorhback Cosasco Inc.) were used during this new series experiment. These probes use carbon steel for both the working and counter electrodes and stainless steel (SS304) as the reference electrode. They were tested in the same corrosion environment described in earlier experiments. Tables 4, 5 and 6 describe the experimental results. As expected, the probes with severe pitting corrosion show $\alpha$ values near 40, intermediate corrosion near 25, and very low uniform corrosion values, near 5.

In accordance with features of the present invention, a new signal processing algorithm is provided to calculate the power spectral density of potential noise level (PSDPNL) during metal corrosion. To complement the new signal process algorithm, the reference electrode of a traditional three-electrode electrochemical noise probe is modified to include a non-corrosive or very corrosion resistant material. The slope of PSDPNL is shown to be very sensitive and can detect rapid localized pitting corrosion with respect to uniform general corrosion.

TABLE 1

Coupon in acid solution or Di-water without coating

| Run / (coupon#) | Counter Electrode | Purging gas | PDS of noise (Average) potential |
|---|---|---|---|
| ECN02_3(4) | S.S. 316 | Air | −3.39 |
| ECN02_2(5) | S.S. 316 | Air | −3.34 |
| ECN09_1(18) | S.S. 316 | Air | −7.16 |
| ECN14_2(29) | G.C. | No | −3.75 |

| Run / (coupon#) | current | Average PI | Average NR |
|---|---|---|---|
| ECN02_3(4) | −12.33 | 1.CGE-04 | 9.89E+03 |
| ECN02_2(5) | −5.42 | 9.77E-05 | 1.56E+04 |
| ECN09_1(18) | −10.54 | 2.63E-02 | 9.83E+03 |
| ECN14_2(29) | −20.345 | 8.65E-05 | 6.53E+04 |

| Run / (coupon#) | Corr. Rate (g/hr) | pH | Morphology |
|---|---|---|---|
| ECN02_3(4) | 1.19E-04 | 3.16 | uniform corrosion |
| ECN02_2(5) | 1.54E-04 | 1.2 | uniform corrosion |
| ECN09_1(18) | 7.48E-05 | 3.5 | uniform corrosion with large number of shallow holes |
| ECN14_2(29) | 9.05E-06 | 6.97 | uniform corrosion without any pits formation on the surface |

TABLE 2

Coupon without coated layer in Di-Water

| Run / (coupon#) | Counter Electrode | Purging gas | PDS of Noise (Average) potential |
|---|---|---|---|
| ECN10-1(20) | S.S. 316 | Air | −40.39 |
| ECN12-1(23) | S.S. 316 | Air | −41.4 |

| Run / (coupon#) | current | Average PI | Average NR |
|---|---|---|---|
| ECN10-1(20) | −38.6 | 4.73E-03 | 3.02E+04 |
| ECN12-1(23) | −25 | 4.44E-03 | 1.76E+03 |

TABLE 2-continued

| Run / (coupon#) | Corr. Rate (g/hr) | pH | Morphology |
|---|---|---|---|
| ECN10-1(20) | 1.08E-06 | 6.95 | 5 deep pits corrosion |
| ECN12-1(23) | 1.08E-05 | 6.95 | "groups" of deep pits corrosion distributed on the coupon |

TABLE 3

Coupon coated with Agar Drop (NaCl + HOAc) in Di-Water

| Run / (coupon#) | Counter Electrode | Purging gas | PDS of Noise (Average) potential |
|---|---|---|---|
| ECN04_2(7) | S.S. 316 | Air | −29.5 |
| ECN06_1(12) | S.S. 316 | Air | −26.5 |
| ECN07_1(14) | S.S. 316 | Air | −24.85 |
| ECN04_1(9) | Pt/Ti | Nz | −30.83 |
| ECN05_2(11) | Pt/Ti | Air | −38.38 |
| ECN06_2(13) | Pt/Ti | Air | −21.00 |
| ECN09_2(19) | Pt/Ti | Air | −23.38 |

| Run /(coupon#) | current | Average PI | Average NR |
|---|---|---|---|
| ECN04_2(7) | −26.05 | 1.39E-02 | 1.35E+04 |
| ECN06_1(12) | −22.5 | 3.27E-04 | 1.69E+04 |
| ECN07_1(14) | −28.45 | 1.10E-03 | 4.31E+04 |
| ECN04_1(9) | −24.91 | 4.22E-04 | 4.26E+03 |
| ECN05_2(11) | −35.30 | 1.17E-03 | 3.07E+03 |
| ECN06_2(13) | −21.00 | 7.06E-04 | 5.46E+03 |
| ECN09_2(19) | −15.26 | 9.41E-01 | 1.60E+03 |

| Run / (coupon#) | Corr. Rate (g/hr) | pH | Morphology |
|---|---|---|---|
| ECN04_2(7) | 2.93E-04 | | major corrosion in the agar are with some pits around the coated area |
| ECN06_1(12) | 8.47E-06 | | major corrosion in the agar coated area with several pits |
| ECN07_1(14) | 8.13E-05 | | localized single-hole deep pits corrosion distributed on the coupon beyond the major corrosion coated area |
| ECN04_1(9) | 7.50E-06 | | major corrosion in the agar area with few pits around the coated area |
| ECN05_2(11) | 4.53E-04 | | large size of pits corrosion inside and outside the coated area |
| ECN06_2(13) | 3.39E-04 | | severe pits and bulk corrosion away from the heavily corroded coated area |
| ECN09_2(19) | 3.51E-04 | No acid added in the Agar | high density of pits in the corrosion area away the coated area |

TABLE 4

Commercial Probes with localized Sustained pitting Corrosion

| | | | PDS of Noise |
|---|---|---|---|
| Run | Corr. Rate | | |

TABLE 4-continued

| Run (probe#) | Time (hours) | Purging gas | (Average) potential |
|---|---|---|---|
| ecn17_1 | 110 | Air | −35.93 |
| ecn18_1 | 96 | No | −35.73 |

| Run (probe#) | current | Average PI | Average NR |
|---|---|---|---|
| ecn17_1 | −17.84 | 8.25E-3 | 7.03E+4 |
| ecn18_1 | −17.88 | 4.05E-2 | 1.17E+7 |

| Run (probe#) | Coated | Morphology |
|---|---|---|
| ecn17_1 | y | Severe localized pitting on both of the working electrodes (50µm depth, 20µm diameter |
| ecn18_1 | y | Severe localized pitting on both of the working electrodes (45µm depth, 15µm diameter) |

TABLE 5

Commercial Probes with Mixing Corrosion

| Run (probe#) | Time (hours) | Purging gas | PDS of Noise (Average) potential |
|---|---|---|---|
| ecn18_2 | 119.00 | No | −24.98 |

| Run (probe#) | current | Average PI | Average NR |
|---|---|---|---|
| ecn18_2 | −36.00 | 4.62E-2 | 7.00E+6 |

| Run (probe#) | Coated | Morphology |
|---|---|---|
| ecn18_2 | n | a few tiny pits on the surface on both of the working electrodes (10µm depth, 5µm diameter) |

TABLE 6

Commercial Probes with Uniform Corrosion

| Run (probe#) | Time (hours) | Purging gas | PDS of Noise (Average) potential |
|---|---|---|---|
| ecn16_1 | 86 | Air | −2.24 |
| ecn17_2 | 110 | Air | −5.32 |

| Run (probe#) | current | Average PI | Average NR |
|---|---|---|---|
| ecn16_1 | −21.34 | 3.79E-4 | 2.33E+4 |
| ecn17_2 | −15.70 | 8.66E-3 | 4.08E+5 |

| Run (probe#) | Coated | Morphology |
|---|---|---|
| ecn16_1 | n | a few tiny pits on the surface on both of the working electrodes (16µm depth, 5µm diameter) |
| ecn17_2 | n | very few small pits formed on the surface (25µm depth, 10µm diameter) |

While the present invention has been described with reference to the details of the embodiments of the invention shown in the drawing, these details are not intended to limit the scope of the invention as claimed in the appended claims.

What is claimed is:

1. Apparatus for monitoring localized pitting corrosion in metal pipes or storage vessels comprising:

electrochemical probe means for sensing electrochemical noise, said electrochemical probe means including a plurality of spaced apart electrodes including a pair of working electrodes and a reference electrode, said pair of working electrodes being formed of the same material as the monitored metal pipes or storage vessels, said reference electrode being formed of a corrosion resistant material;

data acquisition means coupled to said electrochemical probe means for storing sensed electrochemical noise data; said sensed electrochemical noise data including electrochemical voltage noise data and electrochemical current noise data; said data acquisition means including means for calculating root-mean square values of both said electrochemical voltage noise data and said electrochemical current noise data; and data processing means coupled to said data acquisition means for processing said stored electrochemical noise data; said data processing means including Fourier transform means for transforming said stored electrochemical noise data into power spectral density data; and means for calculating a slope of said power spectral density data relative to frequency.

2. Apparatus for monitoring localized pitting corrosion in metal pipes or storage vessels as recited in claim 1 wherein said electrochemical probe means is positioned near the monitored metal pipes or storage vessels.

3. Apparatus for monitoring localized pitting corrosion in metal pipes or storage vessels as recited in claim 1 wherein said electrochemical probe means for sensing electrochemical noise includes a zero-resistance amperometer connecting said pair of working electrodes for providing a current noise signal.

4. Apparatus for monitoring localized pitting corrosion in metal pipes or storage vessels as recited in claim 3 wherein said electrochemical probe means for sensing electrochemical noise includes said reference electrode parallel connected to said pair of working electrodes by a voltage meter, said voltage meter providing a voltage noise signal.

5. Apparatus for monitoring localized pitting corrosion in metal pipes or storage vessels as recited in claim 1 wherein said means for calculating said slope of said power spectral density data relative to frequency includes means for calculating a linear slope of a low-frequency portion of the power spectral density data.

6. Apparatus for monitoring localized pitting corrosion in metal pipes or storage vessels as recited in claim 5 wherein said means for calculating said linear slope of said low-frequency portion of the power spectral density data includes means for linear fitting of said low-frequency portion of the power spectral density data by using a least-square method.

7. Apparatus for monitoring localized pitting corrosion in metal pipes or storage vessels as recited in claim 1 wherein said data acquisition means includes a computer coupled to a potentiostat, said potentiostat arranged as a zero-resistance amperometer and a voltage meter.

8. Apparatus for monitoring localized pitting corrosion in metal pipes or storage vessels as recited in claim 1 wherein said data processing means coupled to said data acquisition means for processing said stored electrochemical noise data includes a computer and program means.

9. A method for monitoring localized pitting corrosion in metal pipes or storage vessels comprising the steps of:

utilizing electrochemical probes and sensing electrochemical noise voltage values and electrochemical noise current values, said electrochemical probes including a plurality of spaced apart electrodes including a pair of working electrodes and a reference electrode, said pair of working electrodes being formed of the same material as the monitored metal pipes or storage vessels, said reference electrode being formed of a corrosion resistant material;

calculating root-mean-square electrochemical noise current and voltage values of the sensed electrochemical noise voltage values and the electrochemical noise current values;

storing said calculated root-mean-square electrochemical noise current and voltage values; and processing said stored electrochemical noise current and voltage values to identify pitting corrosion including the steps of: transforming said stored electrochemical noise current and voltage values into power spectral density data utilizing a fast Fourier transform; and calculating a slope of said power spectral density data relative to frequency.

10. A method for monitoring localized pitting corrosion in metal pipes or storage vessels as recited in claim 9 wherein the step of utilizing electrochemical probes and sensing electrochemical noise voltage values and electrochemical noise current values includes the steps of periodically measuring voltage and current noise values at short time intervals over a long time interval.

11. A method for monitoring localized pitting corrosion in metal pipes or storage vessels as recited in claim 10 wherein said short time intervals are in a range between a number of seconds to a number of minutes and wherein said long time interval is in a range between a number of hours to a number of days.

12. A method for monitoring localized pitting corrosion in metal pipes or storage vessels as recited in claim 9 wherein the step of calculating the slope of said power spectral density data relative to frequency includes the step of calculating a linear slope of a low-frequency portion of the power spectral density data by linear fitting of the low-frequency portion of the power spectral density data by using a least-square method.

* * * * *